(12) United States Patent
Worrel et al.

(10) Patent No.: US 9,145,129 B2
(45) Date of Patent: Sep. 29, 2015

(54) VEHICLE OCCUPANT COMFORT

(71) Applicant: Ford Global Technologies, LLC, Dearborn, MI (US)

(72) Inventors: Peter Francis Worrel, Troy, MI (US); Dale Scott Crombez, Livonia, MI (US); Roger Arnold Trombley, Ann Arbor, MI (US)

(73) Assignee: FORD GLOBAL TECHNOLOGIES, LLC, Dearborn, MI (US)

( * ) Notice: Subject to any disclaimer, the term of this patent is extended or adjusted under 35 U.S.C. 154(b) by 84 days.

(21) Appl. No.: 14/062,094

(22) Filed: Oct. 24, 2013

(65) Prior Publication Data

US 2015/0120149 A1    Apr. 30, 2015

(51) Int. Cl.
| | | |
|---|---|---|
| *B60W 10/30* | (2006.01) | |
| *A61M 21/02* | (2006.01) | |
| *B60H 1/00* | (2006.01) | |
| *B60W 40/08* | (2012.01) | |
| *A61M 21/00* | (2006.01) | |

(52) U.S. Cl.
CPC .............. *B60W 10/30* (2013.01); *A61M 21/02* (2013.01); *B60H 1/00735* (2013.01); *B60H 1/00878* (2013.01); *B60W 40/08* (2013.01); *A61M 2021/005* (2013.01); *A61M 2021/0066* (2013.01); *A61M 2205/332* (2013.01); *A61M 2205/3306* (2013.01); *A61M 2205/3368* (2013.01); *A61M 2205/3375* (2013.01); *A61M 2205/3569* (2013.01); *A61M 2205/3584* (2013.01); *A61M 2205/3592* (2013.01); *A61M 2205/505* (2013.01); *A61M 2205/52* (2013.01); *A61M 2205/80* (2013.01); *B60W 2540/22* (2013.01)

(58) Field of Classification Search
CPC .............. G06F 3/011; H04N 13/0022; H04N 13/0454; H04N 2213/002; G06T 11/00; G09G 2380/08
USPC ........ 701/49, 36; 340/4.13; 348/51; 345/419, 345/589, 629
See application file for complete search history.

(56) References Cited

U.S. PATENT DOCUMENTS

| | | | |
|---|---|---|---|
| 6,623,428 B2 * | 9/2003 | Miller et al. ................... | 600/300 |
| 7,722,526 B2 | 5/2010 | Kim | |
| 7,918,781 B1 * | 4/2011 | Smyth et al. .................... | 600/27 |
| 2005/0159865 A1 * | 7/2005 | Bos ................................. | 701/39 |
| 2006/0015000 A1 * | 1/2006 | Kim ................................ | 600/27 |
| 2006/0125264 A1 * | 6/2006 | Bergeron et al. .......... | 296/24.39 |
| 2008/0062008 A1 * | 3/2008 | Morimoto et al. ............ | 340/936 |
| 2008/0179987 A1 * | 7/2008 | Imazu et al. .................. | 310/218 |
| 2009/0002142 A1 | 1/2009 | Morimoto et al. | |
| 2009/0179987 A1 | 7/2009 | Kim | |
| 2012/0053805 A1 * | 3/2012 | Dantu ............................. | 701/70 |
| 2013/0038599 A1 * | 2/2013 | Krakowski .................... | 345/419 |
| 2013/0197758 A1 | 8/2013 | Ueda et al. | |
| 2014/0218487 A1 * | 8/2014 | Lambert et al. ................. | 348/51 |

OTHER PUBLICATIONS

SITIS Archives—Topic Details, "Reduction of vehicle display-induced motion sickness", SBIR program, A10-126 (Army); 7 pages.
Noor et al., "Automated cars that communicate: How much can that save us in lives, money, and frustration?", Intelligent and Connected, Mechanical Engineering, Nov. 2012, 6 pages.

* cited by examiner

*Primary Examiner* — Marthe Marc-Coleman
(74) *Attorney, Agent, or Firm* — Frank A. MacKenzie; Bejin Bieneman PLC

(57) ABSTRACT

Data is collected related to motion of a vehicle. Based on the collected data, it may be determined that a threshold associated with motion sickness is exceeded. An adjustment for a component in the vehicle may be adjusted based at least in part on the collected data.

17 Claims, 3 Drawing Sheets

VEHICLE OCCUPANT COMFORT

BACKGROUND

Many people experience motion sickness when riding in a vehicle. For example, bumpy or hilly roads, potholes, curves, stop-and-start motion, etc. may cause some people to experience motion sickness. Further, motion sickness may be caused and/or exacerbated for a vehicle occupant by other factors. For example, reading a book, viewing a video, and over-hot climate, etc., may induce or heighten feelings of dizziness, nausea, etc. Attempts to alleviate motion sickness may involve taking medication, not consuming media such as books or video, looking out a window at a distant point, etc. However, further mechanisms for addressing in-vehicle motion sickness are wanting.

DRAWINGS

DESCRIPTION

System Overview

Figure 1:
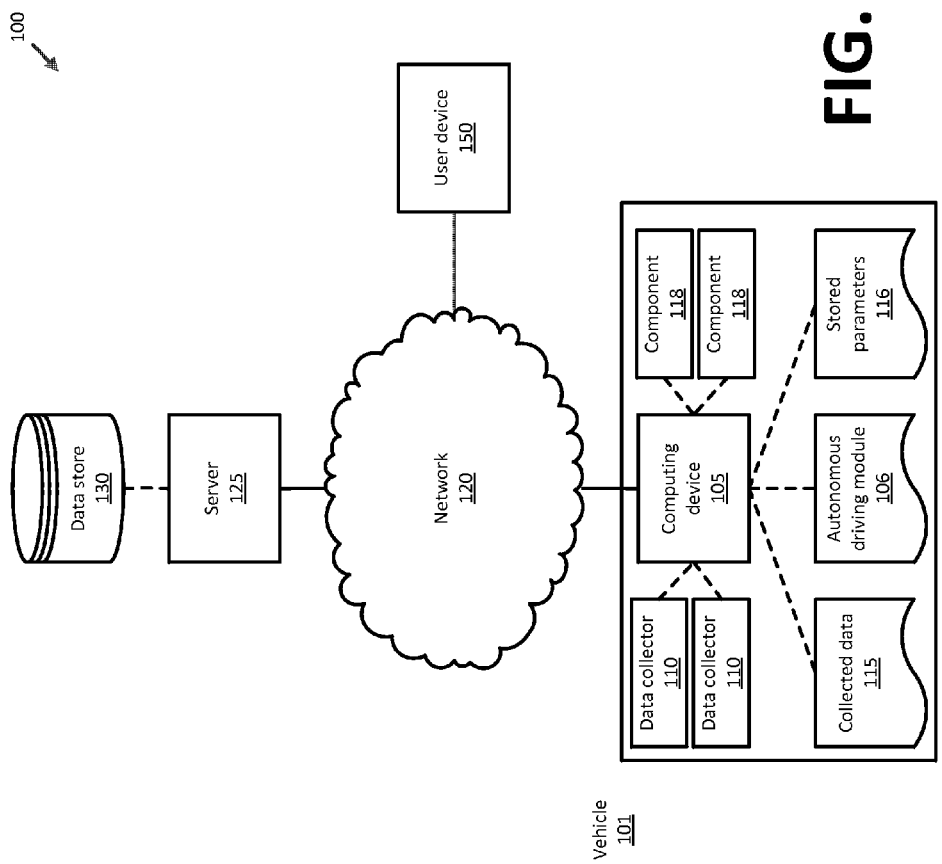
FIG. 1 is a block diagram of an exemplary vehicle system for addressing occupant discomfort including motion sickness.

FIG. 1 is a block diagram of an exemplary vehicle system 100 for addressing occupant discomfort including motion sickness. A vehicle 101 generally includes a computing device 105 that receives collected data 115 from one or more data collectors e.g. sensors, 110. The vehicle 101 possibly, but not necessarily, includes an autonomous driving module 106. In any event, the vehicle computer 105 is configured to evaluate and synchronize collected data 115 and possibly also one or more stored parameters 116 to determine whether to make adjustments to one or more vehicle 101 components 118 to alleviate and/or attempt to prevent vehicle 101 occupant motion sickness. Further, the computer 105 includes instructions for determining adjustments to vehicle 101 components 118, including one or more of a video display in the vehicle 101, a seat or seats in the vehicle 101, vehicle 101 mirrors, a vehicle 101 climate control system, and possibly other components 118. Alternatively or additionally, the computer 105 may include instructions to determine whether to make adjustments to, and to provide adjustments to, a user device 150.

Exemplary System Elements

A vehicle 101 includes a vehicle computer 105 that generally includes a processor and a memory, the memory including one or more forms of computer-readable media, and storing instructions executable by the processor for performing various operations, including as disclosed herein. Further, the computer 105 may include more than one computing device, e.g., controllers or the like included in the vehicle 101 for monitoring and/or controlling various vehicle components, e.g., an engine control unit (ECU), transmission control unit (TCU), etc. The computer 105 is generally configured for communications on a controller area network (CAN) bus or the like. The computer 105 may also have a connection to an onboard diagnostics connector (OBD-II). Via the CAN bus, OBD-II, and/or other wired or wireless mechanisms, the computer 105 may transmit messages to various devices in a vehicle and/or receive messages from the various devices, e.g., controllers, actuators, sensors, etc., including data collectors 110. Alternatively or additionally, in cases where the computer 105 actually comprises multiple devices, the CAN bus or the like may be used for communications between devices represented as the computer 105 in this disclosure.

In addition, the computer 105 may be configured for communicating with the network 120, which, as described below, may include various wired and/or wireless networking technologies, e.g., cellular, Bluetooth, wired and/or wireless packet networks, etc. Further, the computer 105, e.g., in the module 106, generally includes instructions for receiving data, e.g., from one or more data collectors 110 and/or a human machine interface (HMI), such as an interactive voice response (IVR) system, a graphical user interface (GUI) including a touchscreen or the like, etc.

Possibly included in instructions stored in and executed by the computer 105 is an autonomous driving module 106. Using data received in the computer 105, e.g., from data collectors 110, data included as stored parameters 116, the server 125, etc., the module 106 may control various vehicle 101 components and/or operations without a driver to operate the vehicle 101. For example, the module 106 may be used to regulate vehicle 101 speed, acceleration, deceleration, steering, etc.

Data collectors 110 may include a variety of devices. For example, various controllers in a vehicle may operate as data collectors 110 to provide data 115 via the CAN bus, e.g., data 115 relating to vehicle speed, acceleration, etc. Further, sensors or the like, global positioning system (GPS) equipment, etc., could be included in a vehicle and configured as data collectors 110 to provide data directly to the computer 105, e.g., via a wired or wireless connection. Data collectors 110 could also include sensors or the like for detecting conditions outside the vehicle 101, e.g., medium-range and long-range sensors. For example, sensor data collectors 110 could include mechanisms such as RADAR, LADAR, sonar, cameras or other image capture devices, that could be deployed to measure a distance between the vehicle 101 and other vehicles or objects, to detect other vehicles or objects, and/or to detect road conditions, such as curves, potholes, dips, bumps, changes in grade, etc. In addition, data collectors 110 may include sensors internal to the vehicle 101, such as accelerometers, temperature sensors, motion detectors, etc. to detect motion or other conditions of the vehicle 101.

A memory of the computer 105 generally stores collected data 115. Collected data 115 may include a variety of data collected in a vehicle 101 from data collectors 110. Examples of collected data 115 are provided above, and moreover, data 115 may additionally include data calculated therefrom in the computer 105. In general, collected data 115 may include any data that may be gathered by a collection device 110 and/or computed from such data. Accordingly, collected data 115 could include a variety of data related to vehicle 101 operations and/or performance, as well as data related to in particular relating to motion of the vehicle 101. For example, collected data 115 could include data concerning a vehicle 101 speed, acceleration, longitudinal motion, lateral motion, pitch, yaw, roll, braking, etc.

A memory of the computer 105 may further store one or more parameters 116. A parameter 116 generally governs use of collected data 115. For example, a parameter 116 may provide a threshold to which calculated collected data 115 may be compared to determine whether an adjustment should be made to the component 118. Similarly, a parameter 116 could provide a threshold below which an item of collected data 116, e.g., a datum 115 from an accelerometer, should be disregarded.

Vehicle 101 components 118 may include a variety of one or more elements of a vehicle 101. For example, as mentioned above, a component 118 may be a video screen, a seat, a climate control system, a vehicle 101 interior or exterior mirror, etc.

Returning to FIG. 1, the network 120 represents one or more mechanisms by which a vehicle computer 105 may communicate with a remote server 125 and/or a user device 150. Accordingly, the network 120 may be one or more of various wired or wireless communication mechanisms, including any desired combination of wired (e.g., cable and fiber) and/or wireless (e.g., cellular, wireless, satellite, microwave, and radio frequency) communication mechanisms and any desired network topology (or topologies when multiple communication mechanisms are utilized). Exemplary communication networks include wireless communication networks (e.g., using Bluetooth, IEEE 802.11, etc.), local area networks (LAN) and/or wide area networks (WAN), including the Internet, providing data communication services.

The server 125 may be one or more computer servers, each generally including at least one processor and at least one memory, the memory storing instructions executable by the processor, including instructions for carrying out various steps and processes described herein. The server 125 may include or be communicatively coupled to a data store 130 for storing collected data 115 and/or parameters 116. For example, one or more parameters 116 for a particular user could be stored in the server 125 and retrieved by the computer 105 when the user was in a particular vehicle 101. Likewise, collected data 115 concerning adjustments to one or more components 118 could be stored for later evaluation of whether the adjustments were effective in alleviating or preventing vehicle occupant motion sickness.

A user device 150 may be any one of a variety of computing devices including a processor and a memory, as well as communication capabilities. For example, the user device 150 may be a portable computer, tablet computer, a smart phone, etc. that includes capabilities for wireless communications using IEEE 802.11, Bluetooth, and/or cellular communications protocols. Further, the user device 150 may use such communication capabilities to communicate via the network 120 including with a vehicle computer 105. A user device 150 could communicate with a vehicle 101 computer 105 the other mechanisms, such as a network in the vehicle 101, a known protocols such as Bluetooth, etc. Accordingly, a user device 150 may be used to carry out certain operations herein ascribed to a data collector 110, e.g., voice recognition functions, cameras, global positioning system (GPS) functions, etc., in a user device 150 could be used to provide data 115 to the computer 105. Further, a user device 150 could be used to provide a human machine interface (HMI) to the computer 105.

Exemplary Process Flows

Figure 2:
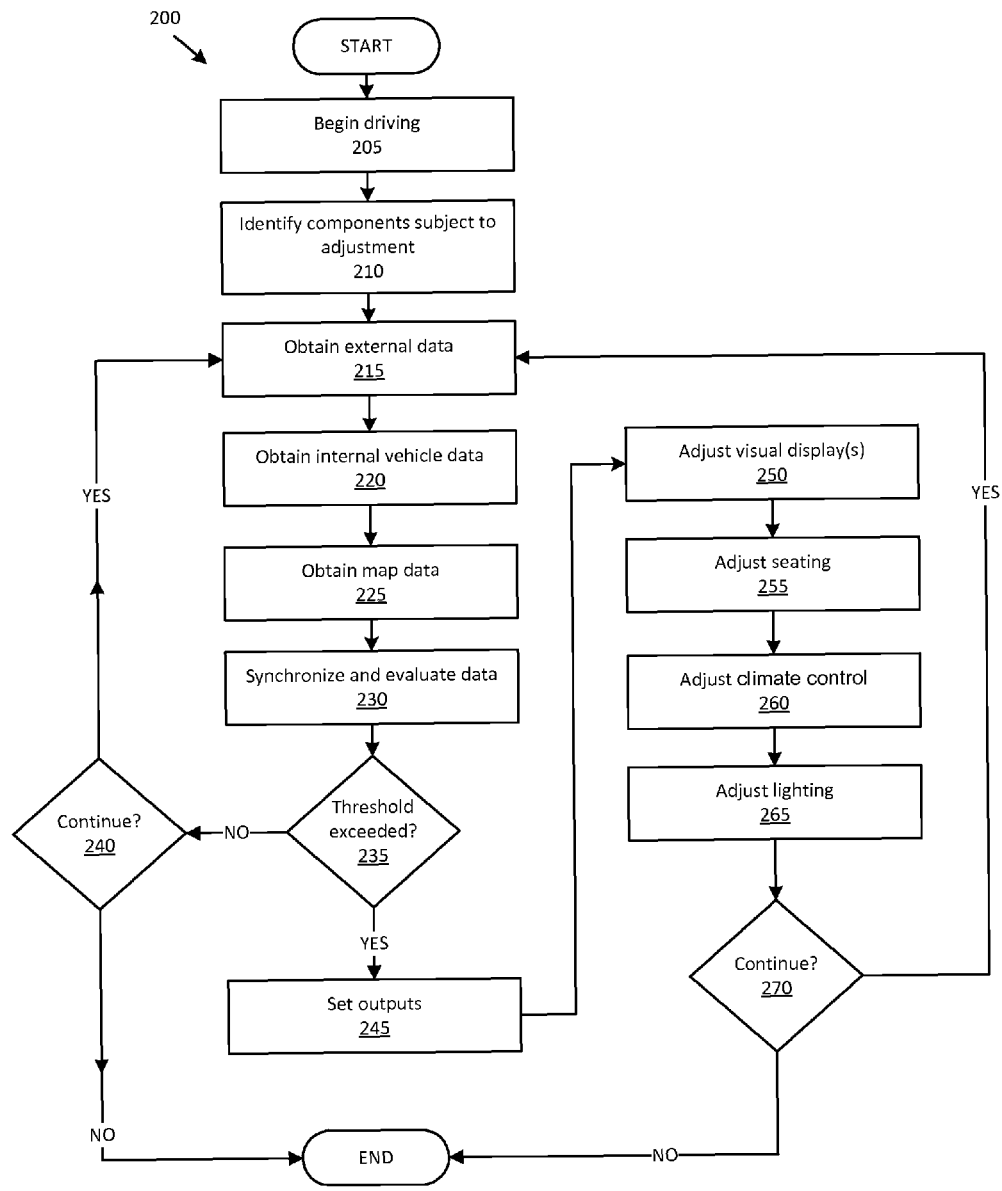
FIG. 2 is a diagram of an exemplary process for addressing vehicle occupant discomfort including motion sickness.

FIG. 2 is a diagram of an exemplary process for addressing vehicle occupant discomfort including motion sickness.

The process 200 begins in a block 205, in which the vehicle 101 commences driving operations. The vehicle 101 could be driven manually by a vehicle occupant, or could be driven autonomously i.e., a manner partially or completely controlled by the autonomous driving module 106. For example, all vehicle 101 operations, e.g., steering, braking, speed, etc., could be controlled by the module 106 in the computer 105. It is also possible that, in the block 205, the vehicle 101 may be operated in a partially autonomous (i.e., partially manual, fashion, where some operations, e.g., braking, could be manually controlled by a driver, while other operations, e.g., including steering, could be controlled by the computer 105. Further, it is possible that the process 200 could be commenced at some point after vehicle 101 driving operations begin, e.g., when manually initiated by a vehicle occupant through a user interface of the computer 105.

Next, in a block 210, the computer 105 identifies components 118 in the vehicle 101 that may be adjusted to attempt to alleviate or prevent occupant motion sickness. For example, instructions could be included in the computer 105 identifying such components 118. Alternatively or additionally, a vehicle 101 occupant could provide input, e.g., through an HMI or user interface of the computer 105, to identify components 118. As mentioned above, vehicle 101 seats, mirrors, climate control systems, video displays, and possibly other elements, may be included as components 118 subject to adjustment. Further, the computer 105 may identify a user device 150 subject to adjustment.

For example, the user device 150 could communicate with the computer 105 via Bluetooth or some other communication mechanism to indicate that the user device 150 is present in the vehicle 101, and may be used in a way, e.g., to play a video presentation, that could contribute to vehicle 101 occupant motion sickness.

Next, in a block 215, the computer 105 obtains external vehicle 101 collected data 115, generally long-range sensor data such as discussed above. Such data may include information concerning road conditions ahead of the vehicle 101, e.g., turns, bumps, dips, etc., as well as data concerning obstacles, other vehicles, etc. that may result in the vehicle 101 changing speed or direction in a manner that could affect motion sickness.

Next, in a block 220, the computer 105 obtains internal vehicle 101 collected data 115. As mentioned above, various types of data collectors 110 may be deployed inside the vehicle 101. For example, accelerometer data collectors 110 may measure pitch, yaw, and roll of a vehicle 101 in an XYZ coordinate system. Likewise, accelerometer data collectors 110 may measure lateral and longitudinal motion of a vehicle 101 in an XY plane oriented as closely as possible to be parallel to a surface on which the vehicle 101 is traveling. Further, internal collected data 115 could be obtained from one or more data collectors 110 mounted on or associated with a component 118. For example, accelerometer data collectors 110 could be mounted on a video display, a seat, etc., in a vehicle 101.

Next, in a block 225, the computer 105 obtains map data related to a route being traveled by the vehicle 101. For example, the computer 105 may store a map of a geographic area in which the vehicle 101 is traveling. Further, a GPS data collector 110 may provide geo-coordinates, e.g., latitude and longitude information, of the vehicle 101. The geo-coordinates may be used to identify a location of the vehicle 101 with respect to the stored map data. Further, the computer 105 may include information concerning a planned route of the vehicle 101 and/or may determine a vehicle 101 short-term anticipated route, e.g., for the next 30 seconds, next two minutes, etc. The computer 105 may then obtain map data related to the anticipated route, e.g., data indicating topographical variation, bends in a road, speed limit changes, etc.

Next, in a block 230, the computer 105 synchronizes and evaluates the collected data 115 obtained from the data collectors 110, e.g., as described above with respect to the blocks 215-225. For example, when synthesizing or fusing collected data 115 from external and internal vehicle 101 data collectors, respectively, it may be necessary to synchronize the data

115. That is, data 115 from a long-range sensor data collector 110 obtained at a same time as data 115 from an internal vehicle 101 accelerometer data collector 110 actually reflect conditions at different times in travel of the vehicle 101. An internal data collector 110 may reflect current conditions of the vehicle 101, whereas data 115 from an external data collector 110 may be used to predict or anticipate conditions of the vehicle 101 at a future point in travel of the vehicle 101, e.g., when the vehicle 101 reaches a point in a roadway where a condition detected by a long-range sensor data collector 110 has been detected.

Further, various items of collected data 115 could be used together to determine whether an adjustment should be made to one or more components 118. Threshold values for one or more items of collected data 115, where exceeding the threshold indicates a likelihood of motion sickness, could be empirically determined, e.g., using a test vehicle 101. For example, an occupant could ride in a vehicle 101, and provide input concerning a degree of motion sickness experienced. Further, such data could be gathered from a large number of vehicle 101 occupant test subjects. Additionally, the test subjects could be wired or otherwise subjected to sensors to detect markers for motion sickness, such as cold sweating. With such data, coupled with GPS coordinates and heading information, a map database identifying locations and/or headings likely to be associated with motion sickness could be created and stored in the data store 130. Accordingly, particular collected datum 115 values and/or combinations of a plurality of collected data 115 values, could be correlated to motion sickness or potential motion sickness in vehicle 101 occupants. For example, approaching a curve of a particular radius at a particular speed may be correlated to increased risk of motion sickness.

Additionally, one or more collected data 115 values could be correlated with alleviating or attempting to alleviate motion sickness via a particular component 118, e.g., a video display, a seat, a mirror, etc. One example of a potential threshold could be based on a combination of a yaw rate and vehicle 101 roll while the vehicle 101 is driving through a curve. Based on test data, a lookup table could be created and stored in the data store 130 relating parameters 116 relating to yaw rate, vehicle roll, curve traversal, etc., to increased risk of motion sickness. Then values of yaw and roll being experienced by a vehicle 101 could be checked against a table of such parameters 116, e.g., downloaded to the computer from the data store 130, stored in a memory of the computer 105, etc., to determine if the thresholds are exceeded. If they are, then appropriate countermeasures, such as disclosed herein, could be taken.

In a block 235, following the block 230, the computer 105 determines whether one or more threshold values determined in the block 230 have been exceeded. For example, the computer 105 could have computed a threshold value in the block 230 for each of a plurality of components 118. In any event, if one or more thresholds have been exceeded, then a block 245 is executed next. Otherwise, a block 240 is executed next.

In the block 240, the computer 105 determines whether the process 200 should continue. For example, a user may provide input to stop the process 200, driving operations of the vehicle 101 could be terminated, or some other input could be provided to stop the process 200. In any event, if the process 200 is determined to continue, then control returns to the block 215. Otherwise, the process 200 ends following the block 240.

In the block 245, which may follow the block 235, the computer 105 determines outputs to, i.e., adjustments to, one or more vehicle 101 components 118. In general, evaluating collected data 115 could involve implementing one or more transfer functions taking as input data 115 concerning vehicle conditions, and providing as output for one or more components 118 to offset (e.g., phase shift 180 degrees) likely to cause motion sickness. Further, the computer 105 is generally configured to establish a magnitude and scale to any adjustments to components 118.

For example, a block 250 could follow the block 245, in which adjustments could be made to a visual display in the vehicle 101. In one example, collected data 115 could indicate that a vehicle 101 was encountering a dip in a roadway at a particular time. For the time when the vehicle 101 was encountering the dip, outputs provided in the block 245 could indicate an adjustment to a video display in the vehicle 101, user device 150, etc., to compensate for the dip. For example, collected data 115 could be evaluated fairly frequently, e.g., every 10 milliseconds, 20 milliseconds, etc. Thus, a video display, a vehicle 101 mirror, etc. could be adjusted at each evaluation to compensate for vehicle 101 motion. When outputs are appropriately scaled as described above in the block 245, adjustments could appear to be relatively minor, or might not be readily noticeable, yet still be effective. For example, an image could be moved from a centered position on a video screen a distance measured in millimeters or less in one or both of an X and a Y direction. Further, such adjustments could be performed with a frequency, e.g., every 10 milliseconds, such that an observer might not notice adjustments. In any case, based on one or more adjustments to a video display, a vehicle 101 occupant viewing such display would be relieved of a sensation of motion that is disconnected from the motion felt through the vehicle 101 that could cause motion sickness.

Further, video could be adjusted, possibly in conjunction with vehicle 101 occupant input, as described further below, to compensate for sensations such as motion sickness induced by a video itself, alone or in combination with motion of the vehicle 101.

Similarly, in a block 255, a vehicle 101 seat could alternatively or additionally be adjusted to relieve a vehicle 101 occupant of a sensation of motion, e.g., a vehicle 101 seat could be moved according to a phase shift to offset vehicle 101 as measured by collected data 115, appropriately scaled. For example, for every movement of the vehicle 101 in an X, Y, or Z direction, a video display or a seat could be moved a respective scaled amount in the X, Y, or Z direction. Likewise, adjustments to an image display and/or a seat could be scaled to lateral or longitudinal movement detected and/or predicted for the vehicle 101. Mechanisms for controlling and actuating seat motion are known, e.g., from vehicle simulators.

The computer 105 could additionally or alternatively determine to make adjustments to vehicle 101 components 118 other than moving a component 118. For example, lighting effects and temperature adjustments are both known to alleviate motion sickness or potential motion sickness. Accordingly, where collected data 115 indicates that the vehicle 101 is experiencing possible motion sickness conditions, in a block 260, vehicle 101 temperature could be adjusted, e.g., a climate control component 118 could be set to cool a cabin temperature of the vehicle 101. Alternatively or additionally, in a block 265, lighting effects, such as modulated lighting in a vehicle 101 cabin providing what is known as a "strobe" effect, could be introduced. Intensity, frequency, and color of lighting modulations could be scaled according to determinations made based on collected data 115 relating to intensity and/or frequency of vehicle 101 motion.

In a block 270, following the block 265, the computer 105 determines whether to continue the process 200, e.g., as described above with respect to the block 240. If so, control returns to the block 215. Otherwise, the process 200 ends.

Figure 3:
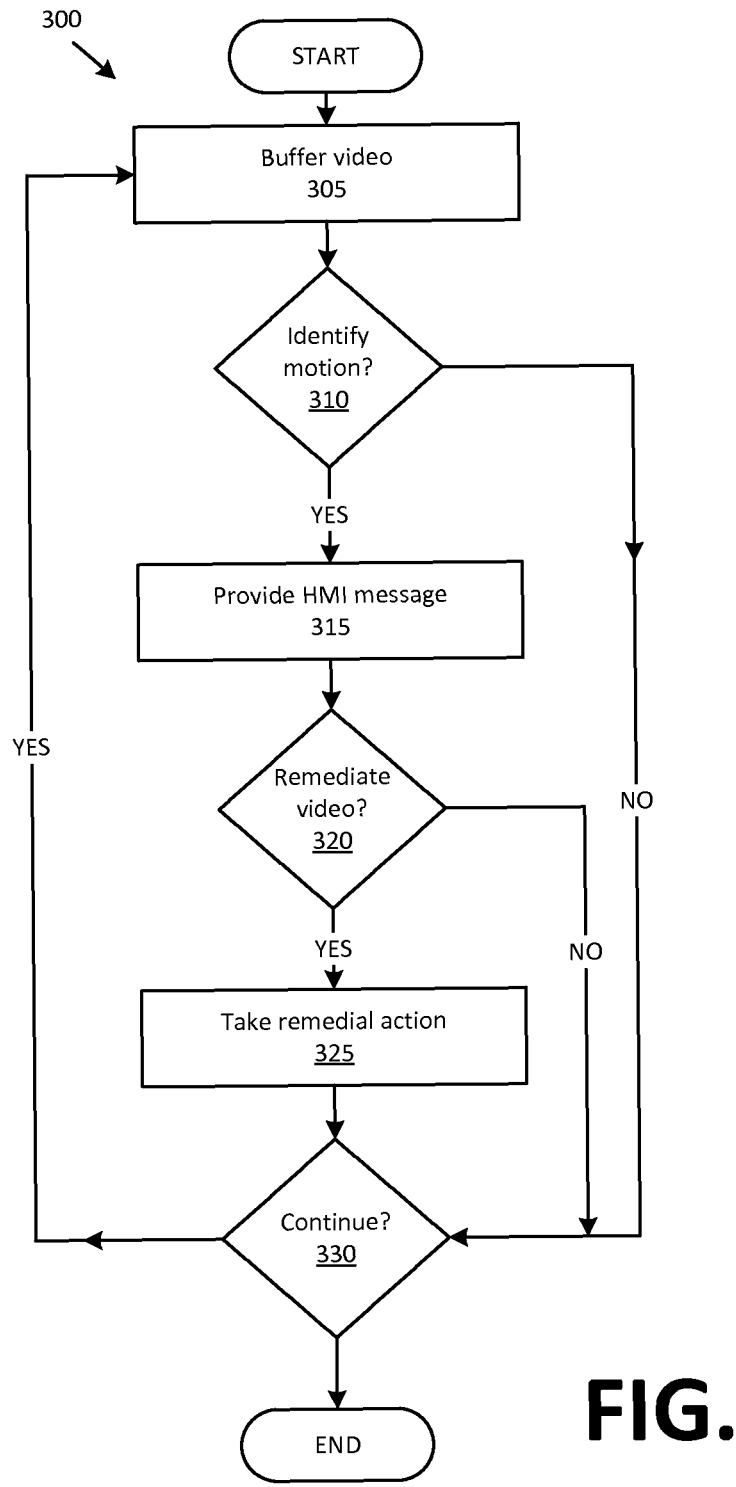
FIG. 3 is a diagram of an exemplary process for controlling a video to address motion sickness.

FIG. 3 is a diagram of an exemplary process for controlling a video to address motion sickness.

The process 300 begins in a block 305, in which the computer 105, being used to provide a display of video data, stores the data in a buffer prior to display on a display device of the computer 105, a user device 150, etc.

Next, in a block 310, the computer 105 uses known image analysis techniques to analyze the video data in the buffer to determine whether it depicts various kinds of motion that may induce a sensation such as motion sickness in a vehicle 101 occupant. For example, a video showing flying, fast driving in a car, views from tall buildings, etc., all may be determined to possibly cause or contribute to motion sickness. If motion and/or other images and/or phenomena in the buffered video data are determined to possibly contribute to motion sickness, then a block 315 is executed next. Otherwise, the process 300 proceeds to a block 330.

In the block 315, the computer 105 pauses the video being played. Further, in some implementations, the computer 105 provides an HMI message, e.g., an interactive voice response message, a textual message on a display screen of the computer 105, etc., indicating that the video being played may contribute to motion sickness. The computer 105 then requests that the vehicle 101 occupant provide input indicating whether remedial action should be taken with respect to the video being played. Moreover, the occupant may be asked to provide input concerning a type of remedial action to be taken, e.g., skip a portion of video likely to contribute to motion sickness altogether, omit a video portion likely to contribute to motion sickness but include a related audio portion, play the audio file as normal while displaying freeze-framed images from the video feed, etc. In some implementations, the computer 105, instead of pausing the video being played, may provide such HMI message sufficiently in advance of a portion of the video likely to cause motion sickness so as to provide the vehicle 101 occupant time to provide the input. In yet further implementations, and HMI message may not be provided, but instead the computer 105 includes instructions concerning remedial action to be taken.

Next, in a block 320, the computer 105 determines whether remedial action is to be taken concerning a video being played. For example, user input could be received as described above with respect to the block 315, or the computer 105 could include a predetermined instructions concerning remedial action to take. In any event, if remedial action is not to be taken, then the process 300 proceeds to the block 330. Otherwise, they block 325 is executed next.

In the block 325, the computer 105 implements a remedial action with respect to a portion of video being played in the vehicle 101, such portion of video having been determined as likely to contribute to motion sickness. For example, as mentioned above, the computer 105 could play only audio associated with the portion of video, without showing any images, or could skip the portion of the video altogether.

In the block 330, which may follow any of the blocks 310, 320, or 325, the computer 105 determines whether the process 300 should continue. For example, a video may end, a user could provide input to end the process 300, etc. If the process 300 should continue, control returns to the block 305. Otherwise, the process 300 ends.

Note that the process 300 could be carried out in conjunction with the process 200. That is, the computer 105 could monitor vehicle 101 motion and/or expected motion, and at the same time monitor a video being played in the vehicle 101. In some cases, a threshold to determine whether a video being played in the vehicle 101 could contribute to motion sickness could be adjusted according to whether a threshold is exceeded as described above with respect to the block 235, that is, adjustments to video being played in the vehicle 101 could be adjusted according to a degree of motion or expected motion of the vehicle 101.

CONCLUSION

Computing devices such as those discussed herein generally each include instructions executable by one or more computing devices such as those identified above, and for carrying out blocks or steps of processes described above. For example, process blocks discussed above may be embodied as computer-executable instructions.

Computer-executable instructions may be compiled or interpreted from computer programs created using a variety of programming languages and/or technologies, including, without limitation, and either alone or in combination, Java™, C, C++, Visual Basic, Java Script, Perl, HTML, etc. In general, a processor (e.g., a microprocessor) receives instructions, e.g., from a memory, a computer-readable medium, etc., and executes these instructions, thereby performing one or more processes, including one or more of the processes described herein. Such instructions and other data may be stored and transmitted using a variety of computer-readable media. A file in a computing device is generally a collection of data stored on a computer readable medium, such as a storage medium, a random access memory, etc.

A computer-readable medium includes any medium that participates in providing data (e.g., instructions), which may be read by a computer. Such a medium may take many forms, including, but not limited to, non-volatile media, volatile media, etc. Non-volatile media include, for example, optical or magnetic disks and other persistent memory. Volatile media include dynamic random access memory (DRAM), which typically constitutes a main memory. Common forms of computer-readable media include, for example, a floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH-EEPROM, any other memory chip or cartridge, or any other medium from which a computer can read.

In the drawings, the same reference numbers indicate the same elements. Further, some or all of these elements could be changed. With regard to the media, processes, systems, methods, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating certain embodiments, and should in no way be construed so as to limit the claimed invention.

Accordingly, it is to be understood that the above description is intended to be illustrative and not restrictive. Many embodiments and applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future embodiments. In sum, it should be understood that the invention is capable of modification and variation and is limited only by the following claims.

All terms used in the claims are intended to be given their broadest reasonable constructions and their ordinary meanings as understood by those skilled in the art unless an explicit indication to the contrary in made herein. In particular, use of the singular articles such as "a," "the," "said," etc. should be read to recite one or more of the indicated elements unless a claim recites an explicit limitation to the contrary.

The invention claimed is:

1. A system, comprising a computer, the computer comprising a processor and a memory, wherein the computer is configured to:
    collect motion data that indicates motion of a vehicle;
    determine a likelihood that a video being played in the vehicle will cause motion sickness;
    determine, based on the collected motion data and the likelihood that the video will cause motion sickness, that a threshold associated with motion sickness is exceeded; and
    output an adjustment for at least one component in the vehicle based on the threshold being exceeded, wherein the at least one component includes a component unrelated to a video display.

2. The system of claim 1, wherein the at least one component includes one of a mirror, a seat, a light, and a climate control system.

3. The system of claim 2, wherein the at least one component further includes the video display, whereby the adjustment is to at least the video display and also to the component unrelated to the video display.

4. The system of claim 1, wherein the computer is further configured to determine that a plurality of thresholds associated with motion sickness are exceeded.

5. The system of claim 1, wherein the computer is further configured to output an adjustment for each of a plurality of components in the vehicle.

6. The system of claim 1, wherein the collected data includes geo-coordinates for the vehicle.

7. The system of claim 1, wherein the threshold is specified at least in part according to data correlating a likelihood of motion sickness to data collected in a test vehicle.

8. The system of claim 1, wherein the at least one component includes a video display provided to play the video in the vehicle, and the computer is further configured to output an adjustment for the at least one component in the vehicle based at least in part on analyzing video being provided to the display.

9. The system of claim 8, wherein the computer is further configured to request user input to confirm that playback of the video stream should be adjusted.

10. A method, comprising:
    collecting motion data that indicates motion of the vehicle;
    determining a likelihood that a video being played in the vehicle will cause motion sickness;
    determining, based on the collected motion data and the likelihood that the video will cause motion sickness, that a threshold associated with motion sickness is exceeded; and
    outputting an adjustment for at least one component in the vehicle based on the threshold being exceeded, wherein the at least one component includes a component unrelated to a video display.

11. The method of claim 10, wherein the at least one component further includes one of a mirror, a seat, a light, and a climate control system.

12. The method of claim 11, wherein the at least one component further includes the video display, whereby the adjustment is to at least the video display and also to the component unrelated to the video display.

13. The method of claim 10, further comprising determining that a plurality of thresholds associated with motion sickness are exceeded.

14. The method of claim 10, further comprising outputting an adjustment for each of a plurality of components in the vehicle.

15. The method of claim 10, wherein the collected data includes geo-coordinates for the vehicle.

16. The method of claim 10, wherein the threshold is specified at least in part according to data correlating a likelihood of motion sickness to data collected in a test vehicle.

17. The method of claim 10, wherein the at least one component includes a video display provided to play the video in the vehicle, and the computer is further configured to output an adjustment for the at least one component in the vehicle based at least in part on analyzing video being provided to the display.

* * * * *